US007223579B2

(12) United States Patent
Van Der Geize et al.

(10) Patent No.: US 7,223,579 B2
(45) Date of Patent: May 29, 2007

(54) IDENTIFICATION OF 3-KETOSTEROID 9-ALFA-HYDROXYLASE GENES AND MICROORGANISMS BLOCKED IN 3-KETOSTEROID 9-ALFA-HYDROXYLASE ACTIVITY

(75) Inventors: Robert Van Der Geize, Veendam (NL); Peter Van Der Meijden, Oss (NL); Gerda Hessels, Groningen (NL); Lubbert Dijkhuizen, Zuidlaren (NL)

(73) Assignee: N.V. Organon, Oss (NL)

( * ) Notice: Subject to any disclaimer, the term of this patent is extended or adjusted under 35 U.S.C. 154(b) by 90 days.

(21) Appl. No.: 10/504,034

(22) PCT Filed: Feb. 19, 2003

(86) PCT No.: PCT/EP03/50025

§ 371 (c)(1),
(2), (4) Date: Aug. 5, 2004

(87) PCT Pub. No.: WO03/070925

PCT Pub. Date: Aug. 28, 2003

(65) Prior Publication Data

US 2006/0040343 A1    Feb. 23, 2006

(30) Foreign Application Priority Data

Feb. 21, 2002    (EP)    .................................. 02075723

(51) Int. Cl.
*C12N 9/04*    (2006.01)
*C07H 21/04*    (2006.01)
(52) U.S. Cl. ...................................... 435/190; 536/23.2
(58) Field of Classification Search .................. 435/52, 435/58, 7.32, 320.1, 69.1
See application file for complete search history.

(56) References Cited

FOREIGN PATENT DOCUMENTS

WO    WO 01/31050 A1    5/2001

OTHER PUBLICATIONS

Targeted Disruption of the kstD Gene Encoding a 3-Ketosteroid 1-Dehydrogenase Isoenzyme of *Rhodococcus erythropolis* Strain SQ1. Applied and Environmental Microbiology, May 2000, p. 2029-2036, vol. 66, No. 5.*
Kosono et al or Maeda et al. Three of the seven bphC genes of *Rhodococcus erythropolis* TA41, isolated from a termite ecosystem, are located onan indigenous plasmid associated with biphenyl degradation. Applied and environmental Microbiology. Aug. 1997, p. 3282-3285. see accession No. D88013.*
Lipman et al., "Rapid and Sensitive Protein Similarity Searches," Science, vol. 227, pp. 1435-1141, (Mar. 22, 1985).
Dutta et al., "Role of plasmid pJL1 of *Arthrobacter oxydans* 317 in the degradation of β-sitosterol," J. Basic Microbiol., vol. 32, No. 5, pp. 317-324 (1992).
Strijewski, "The Steroid-9α-Hydroxylation System from *Nocardia* Species," Eur. J. Biochem., vol. 128, pp. 125-135 (1982).
Chang et al., "Mechanisms of Steroid Oxidation by Microorganisms." VII. Properties of the 9α-Hydroxylase, vol. 3, No. 10, pp. 1551-1557 (Oct. 1964).
Mahato et al., "Advances in microbial steroid biotransformation," Steroids vol. 62, pp. 332-345 (Apr. 1997).
Wovcha et al., "Bioconversion Of Sitosterol To Useful Steroidal Intermediates By Mutants Of *Mycobacterium fortuitum*," Biochemica et Biophysica Acta, vol. 531 pp. 308-321 (1978).
Datcheva et al., "Synthesis Of 9α-Hydroxysteroids By A *Rhodococcus* Sp.," Steroids, vol. 54, No. 3, pp. 271-286 (Sep. 1989).
Van der Geize et al., "Unmarked gene deletion mutagenesis of kstD, encoding 3-ketosteroid Δ¹-dehydrogenase, in *Rhodococcus erythropolis* SQ1 using sacB as counter-selectable marker," FEMS Microbiology Letters 205, pp. 197-202 (2001).
Maeda et al., "Multiple Genes Encoding 2,3-Dihydroxybiphenyl 1,2-Dioxygenase in the Gram-Positive Polychlorinated Biphenyl-Degrading Bacterium *Rhodococcus erythropolis* TA421, Isolated from a Termite Ecosystem," Applied and Environmental Microbiology, vol. 61, No. 2, pp. 549-555 (Feb. 1995).
Vogt Singer et al., "Construction of an *Escherichia coli-Rhodococcus* Shuttle Vector and Plasmid Transformation in *Rhodococcus* spp.," Journal Of Bacteriology, vol. 170, No. 2, pp. 638-645 (Feb. 1988).
Jager et al., "Expression of the *Bacillus subtilis* sacB Gene Leads to Sucrose Sensitivity in the Gram-Positive Bacterium *Corynebacterium glutamicum* but Not in *Streptomyces lividans*," Journal of Bacteriology, vol. 174, No. 16, pp. 5462-5465 (Aug. 1992).

(Continued)

*Primary Examiner*—Kathleen M. Kerr
*Assistant Examiner*—Kagnew Gebreyesus
(74) *Attorney, Agent, or Firm*—F. Aaron Dubberley (57) ABSTRACT

The invention relates to an isolated polynucleotide sequence comprising a nucleic acid sequence encoding the amino acid sequence of KshA protein or of KshB protein, encoded by nucleotides 499–1695 of SEQ ID NO: 1 or by nucleotides 387–1427 of SEQ ID NO:2, respectively, and functional homologues thereof. The polynucleotides of the invention can be used to construct genetically modified microorganisms blocked in 3-ketosteroid 9α-hydroxylase activity, which are useful in the microbial degradation of steroids to accumulate certain steroid products.

4 Claims, 4 Drawing Sheets

OTHER PUBLICATIONS

Cole et al., "Deciphering the biology of *Mycobacterium tuberculosis* from the complete genome sequence," Nature, vol. 393, pp. 537-544 (1998).

Thompson et al., "Clustal W: improving the sensitivity of progressive multiple sequence alignment through sequence weighting, position-specific gap penalties and weight matrix choice," Nucleic Acids Research, vol. 22, No. 22, pp. 4673-4680 (1994).

Kieslich, "Microbial side-chain degradation of sterols$_1$," J. Basic Microbiol., vol. 25, No. 7, pp. 461-474 (1985).

AF096929 Database EMBL 'Online!, (2000).

Van Der Geize R. et al "Targeted Disruption of the kstD Gene Encoding . . . "Applied and Environmental Microbio. ,May 2000, US, V66 N5 P 2029-2036, XP002157019.

Database EMBL 'Online!, *Rhodococcus* oxygenase reductase KshB, Jun. 3, 2002, XP002249468.

Van Der Geize R et al "Molecular and functional characterization of kshA and kshB, encoding two components of 3-ketosteroid 9alpha-hydroxylase, a class IA . . . " Molecular Microbio.

Database D88013 'Online! EMBl; oxygenase, Apr. 18, 1998 XP002207042.

Database EMBL 'Online! *Rhodococcus erythropolis* terminal oxygenase KshA, Jun. 3, 2004 XP002249469.

Database EMBL'Online "DszD utlization in desulfurizaiton of DBT . . . " Gray Sep. 29, 1999, XP002264155.

\* cited by examiner

IDENTIFICATION OF 3-KETOSTEROID 9-ALFA-HYDROXYLASE GENES AND MICROORGANISMS BLOCKED IN 3-KETOSTEROID 9-ALFA-HYDROXYLASE ACTIVITY

RELATED APPLICATION

This application is the US national stage filing of application number PCT/EP03/50025, filed on Feb. 19, 2003.

FIELD OF THE INVENTION

The invention relates to isolated polynucleotide sequences encoding 3-ketosteroid 9α-hydroxylase components, to microorganisms blocked in 3-ketosteroid 9α-hydroxylase activity, to a method for the preparation of said microorganisms, and to the use of such microorganisms in steroid $\Delta^1$-dehydrogenation.

BACKGROUND OF THE INVENTION

To date very limited knowledge is available on 3-ketosteroid 9α-hydroxylase (KSH), the enzyme performing the 9α-hydroxylation of 4-androstene-3,17-dione (AD) and 1,4-androstadiene-3,17-dione (ADD) in microbial sterol/steroid degradation. No nucleotide sequences of the genes encoding KSH components have been reported. Furthermore, difficulties are faced during enzyme purification procedures (Chang, F. N. et al. Biochemistry (1964) 3:1551–1557; Strijewski, A. Eur. J. Biochem. (1982) 128:125–135). A three-component monooxygenase with KSH activity has been partially purified from *Nocardia* sp. M117 and was found to constitute a three-component enzyme system, composed of a flavoprotein reductase and two ferredoxin proteins (Strijewski, A. Eur. J. Biochem. (1982) 128:125–135). In *Arthrobacter oxydans* 317, 9α-hydroxylation of the steroid poly-cyclic ring structure appeared plasmid-borne (Dutta, R. K. et al. J. Basic Microbiol. (1992) 32:317–324). Nucleotide sequence analysis of the plasmid, however, was not reported.

The lack of genetic data has hampered the construction of molecularly defined mutant strains with desired properties (i.e. blocked 9α-hydroxylation of steroids) by genetic engineering. Mutants have been isolated by classical mutagenesis, but these strains usually are inadequate in industrial processes mostly due to genetic instability and/or low bioconversion efficiencies. Molecularly defined mutants have advantages compared to mutants generated by classical mutagenesis. The constructed mutants are genetically stable and the introduced mutations are well-defined genetic modifications. Construction of genetically engineered strains make the widespread use of chemical agents to block 9α-hydroxylation (e.g. α,α-dipyridyl, o-phenanthroline) obsolete. Chemical agents used to block KSH activity mostly are not reaction specific and inhibit other important enzymatic reactions (e.g. sterol 26-hydroxylation in sterol side chain degradation), which may have negative effects on sterol bioconversion efficiency. The use of defined mutants by genetic engineering overcomes these problems.

3-Ketosteroid 9α-hydroxylase (KSH) is a key-enzyme in the microbial steroid ring B-opening pathway. KSH catalyzes the conversion of AD into 9α-hydroxy-4-androstene-3,17-dione (9OHAD) and ADD into the chemically unstable compound [9OHADD]. KSH activity has been found in many bacterial genera (Martin, C. K. A. Adv. Appl. Microbiol. (1977) 22: 29–58; Kieslich, K. J Basic Microbiol. (1985)25: 461–474; Mahato, S. B. et al. Steroids (1997)62: 332–345): e.g. *Rhodococcus* (Datcheva, V. K. et al. Steroids (1989) 54:271–286; Van der Geize et al. FEMS Microbiol. Lett. (2001) 205: 197–202, *Nocardia* (Strijewski, A. Eur. J. Biochem. (1982) 128:125–135), *Arthrobacter* (Dutta, R. K. et al. J. Basic Microbiol. (1992)32:317–324) and *Mycobacterium* (Wovcha, M. G. et al. Biochim Biophys Acta (1978) 531:308–321). Bacterial strains lacking KSH activity are being considered important in sterol/steroid biotransformation. Mutants blocked in KSH activity will be able to perform only the KSTD (3-ketosteroid $\Delta^1$-dehydrogenase) reaction, thereby allowing selective $\Delta^1$-dehydrogenation of steroid compounds. Examples are the cortisol biotransformation into prednisolone and the AD biotransformation into ADD. Sterol bioconversion by mutants blocked at the level of steroid 9α-hydroxylation may also carry out a selective degradation of the sterol side chain thereby accumulating AD and/or ADD which are excellent precursors for the synthesis of bioactive steroid hormones.

SUMMARY OF THE INVENTION

According to one aspect of the present invention, the isolated polynucleotide sequences of two genes, designated kshA and kshB of *Rhodococcus erythropolis* are now provided: SEQ ID NO:1 and SEQ ID NO:2, respectively. KshA protein is encoded by nucleotides 499–1695 of SEQ ID NO:1 and KshB protein by nucleotides 387–1427 of SEQ ID NO:2. Thus, in particular preferred are polynucleotides comprising the complete coding DNA sequences of the nucleotides 499–1695 of SEQ ID NO:1 and of the nucleotides 387–1427 of SEQ ID NO:2, respectively.

Furthermore, to accommodate codon variability the invention also includes sequences coding for the same amino acid sequences of the KshA protein and the KshB protein. Also portions of the coding sequences coding for individual domains of the expressed protein are part of the invention as well as allelic and species variations thereof. Sometimes, a gene is expressed as a splicing variant, resulting in the inclusion of an additional exon sequence, or the exclusion of an exon. Also a partial exon sequence may be included or excluded. A gene may also be transcribed from alternative promotors that are located at different positions within a gene, resulting in transcripts with different 5' ends. Transcription may also terminate at different sites, resulting in different 3' ends of the transcript. These sequences as well as the proteins encoded by these sequences all are expected to perform the same or similar functions and form also part of the invention. The sequence information as provided herein should not be so narrowly construed as to require inclusion of erroneously identified bases. The specific sequence disclosed herein can be readily used to isolate the complete genes which in turn can easily be subjected to further sequence analyses thereby identifying sequencing errors.

The present invention further relates to polynucleotides having slight variations or having polymorphic sites. Polynucleotides having slight variations encode polypeptides which retain the same biological function or activity as the natural, mature protein.

DETAILED DESCRIPTION OF THE INVENTION

The DNA according to the invention may be obtained from cDNA using suitable probes derived from SEQ ID NO:1 or SEQ ID NO:2. Alternatively, the coding sequence might be genomic DNA, or prepared using DNA synthesis techniques. The polynucleotide may also be in the form of RNA. If the polynucleotide is DNA, it may be in single stranded or double stranded form The single strand might be the coding strand or the non-coding (anti-sense) strand.

The present invention further relates to polynucleotides which have at least 70%, preferably 80%, more preferably 90%, even more preferred 95%, and highly preferably 98% and most preferred at least 99% identity with the entire DNA sequence of the nucleotides 499–1695 of SEQ ID NO:1 and of the nucleotides 387–1427 of SEQ ID NO:2, respectively. Such polynucleotides encode polypeptides which retain the same biological function or activity as the natural, mature protein. Alternatively, also fragments of the above mentioned polynucleotides which code for domains of the protein which still are capable of binding to substrates are embodied in the invention.

The percentage of identity between two sequences can be determined with programs such as Clustal W 1.7 (Thompson J. D., et al. Nucleic Acids Res. (1994) 22: 4673–4680: "CLUSTALW: improving the sensitivity of progressive multiple sequence alignment through sequence weighing, position-specific gap penalties and weight matrix.") used in default settings. The percentage identity generally is defined by the number of identical residues between the two sequences divided by the total number of residues of the known sequence.

Similarity is defined as a combination of identity together with all semi-conserved amino acid residues in the alignment according to the groups as defined in ClustalW 1.7:
'*'=identity=indicates positions which have a single, fully conserved residue
':'=semi-conserved=indicates that one of the following 'strong' groups is fully conserved. STA, NEQK, NHQK, NDEQ, QHRK, MILV, MILF, HY, FYW.
'.'=semi-conserved=indicates that one of the following 'weaker' groups is fully conserved. CSA, ATV, SAG, STNK, STPA, SGND, SNDEQK, NDEQHK, NEQHRK, FVLIM, HFY.

These are all the positively scoring groups that occur in the Gonnet Pam250 matrix.

Also within the scope of this invention are functional homologues of the new genes e.g. in the family of Actinomycetales (e.g. *Rhodococcus, Nocardia, Arthrobacter, Corynebacterium* and *Mycobacterium*).

In order to identify such genes with similar action in other microorganisms, any method for detection of (poly)nucleotides known in the art for such purpose is included herewith. For example, nucleotide elongation methods/amplification methods may be considered, but also, such method may comprise the steps of: hybridizing to a sample a probe specific for a polynucleotide encoding an amino acid sequence of KshA or KshB under conditions effective for said probe to hybridize specifically to said polynucleotide and determining the hybridization of said probe to polynucleotides in said sample. The term "specific" in this respect means that the majority of hybridization takes place with a polynucleotide of this invention. Preferably, said probe comprises at least 25 of the nucleotides of SEQ ID NO:1 or SEQ ID NO:2. More preferred, the probe comprises 50, and in particular preferred more than 100, nucleotides of SEQ ID NO:1 or SEQ ID NO:2. Most preferred, the probe consists of a polynucleotide of nucleotides selected from the nucleotides 499–1695 of SEQ ID NO:1 and of the nucleotides 387–1427 of SEQ ID NO:2, respectively. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1–6.3.6. For example, the salt concentration in the wash step can be selected from low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

Alternatively, the polynucleotides of this invention may also be used for targeting specific genes, e.g. for the purpose of gene disruption in other species (see for example WO 01/31050 and references cited therein).

The sequence of the newly identified polynucleotide of the present invention, SEQ ID NO:1 and SEQ ID NO:2 may also be used in the preparation of vector molecules for the expression of the encoded protein in suitable host cells. A wide variety of host cell and cloning vehicle combinations may be usefully employed in cloning the nucleic acid sequences coding for the proteins KshA or KshB or parts thereof. For example, useful cloning vehicles may include chromosomal, non-chromosomal and synthetic DNA sequences such as various known bacterial plasmids and wider host range plasmids and vectors derived from combinations of plasmids and phage or virus DNA. Vehicles for use in expression of the polynucleotides of the present invention or a part thereof comprising a functional domain will further comprise control sequences operably linked to the nucleic acid sequence coding for the protein. Such control sequences generally comprise a promoter sequence and sequences which regulate and/or enhance expression levels. Of course control and other sequences can vary depending on the host cell selected.

Suitable expression vectors are for example bacterial or yeast plasmids, wide host range plasmids and vectors derived from combinations of plasmid and phage or virus DNA. Vectors derived from chromosomal DNA are also included. Furthermore an origin of replication and/or a dominant selection marker can be present in the vector according to the invention. The vectors according to the invention are suitable for transforming a host cell. Integrative vectors may also be regarded as suitable expression vehicles.

Recombinant expression vectors comprising DNA of the invention as well as cells transformed with said DNA or said expression vector also form part of the present invention.

Suitable host cells according to the invention are bacterial host cells, yeast and other fungi, insect, plant or animal host cells such as Chinese Hamster Ovary cells or monkey cells or human cell lines. Thus, a host cell which comprises DNA or expression vector according to the invention is also within the scope of the invention. The engineered host cells can be cultured in conventional nutrient media which can be modified e.g. for appropriate selection, amplification or induction of transcription. The culture conditions such as temperature, pH, nutrients etc. are well known to those ordinary skilled in the art.

The techniques for the preparation of DNA or the vector according to the invention as well as the transformation or transfection of a host cell with said DNA or vector are standard and well known in the art, see for instance Sambrook et al., Molecular Cloning: A laboratory Manual. 2nd Ed., Cold Spring Harbor Laboratory, Cold Spring Harbor, N.Y., 1989.

In another aspect of the invention, there is provided for a protein comprising the amino acid sequence encoded by any of the above described DNA molecules. Preferably, the protein according to the invention comprises an amino acid sequence encoded by the nucleotides 499–1695 of SEQ ID NO:1 or of the nucleotides 387–1427 of SEQ ID NO:2, respectively. Also part of the invention are proteins resulting from post translational processing, which proteins are encoded by the polynucleotide of this invention.

Also functional equivalents, that is proteins homologous to amino acid sequences of KshA and KshB or parts thereof having variations of the sequence while still maintaining functional characteristics, are included in the invention.

The variations that can occur in a sequence maybe demonstrated by (an) amino acid difference(s) in the overall sequence or by deletions, substitutions, insertions, inversions or additions of (an) amino acid(s) in said sequence. Amino acid substitutions that are expected not to essentially alter biological activities, have been described. Amino acid replacements between related amino acids or replacements which have occurred frequently in evolution are, inter alia Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Based on this information Lipman and Pearson developed a method for rapid and sensitive protein comparison (Science, 1985, 227,1435–1441) and determining the functional similarity between homologous polypeptides. It will be clear that also polynucleotides coding for such variants are part of the invention.

The polypeptides according to the present invention also include polypeptides comprising an amino acid sequence encoded by the nucleotides 499–1695 of SEQ ID NO:1 or of the nucleotides 387–1427 of SEQ ID NO:2, respectively, but further polypeptides with a similarity of at least 70%, preferably 80%, more preferably 90%, and even more preferred 95%. Also portions of such polypeptides still capable of conferring biological effects are included.

Another aspect of the present invention are genetically modified microorganisms. For the construction of mutant strains incapable of 9α-hydroxylation, the genes encoding KSH activity must be identified and their nucleotide sequence must be known. The two genes of this invention, designated kshA and kshb, were identified in *Rhodococcus erythropolis* SQ1 to encode KSH. These genes were cloned by functional complementation of two UV mutants, designated strains RG1-UV26 and RG1-UV39, both impaired in 9α-hydroxylation of AD(D). They were isolated via an extensive screening of UV irradiated cells of *R. erythropolis* strain RG1 (van der Geize, R. et al. FEMS Microbiol. Lett. Submitted 2001), a kstD (encoding 3-ketosteroid $\Delta^1$-dehydrogenase=KSTD1) gene deletion mutant of strain SQ1. Strains RG1-UV26 and RG1-UV39 were unable to grow on AD and ADD, but grew normally on 9OHAD, indicating deficient KSH activity.

Figure 1:
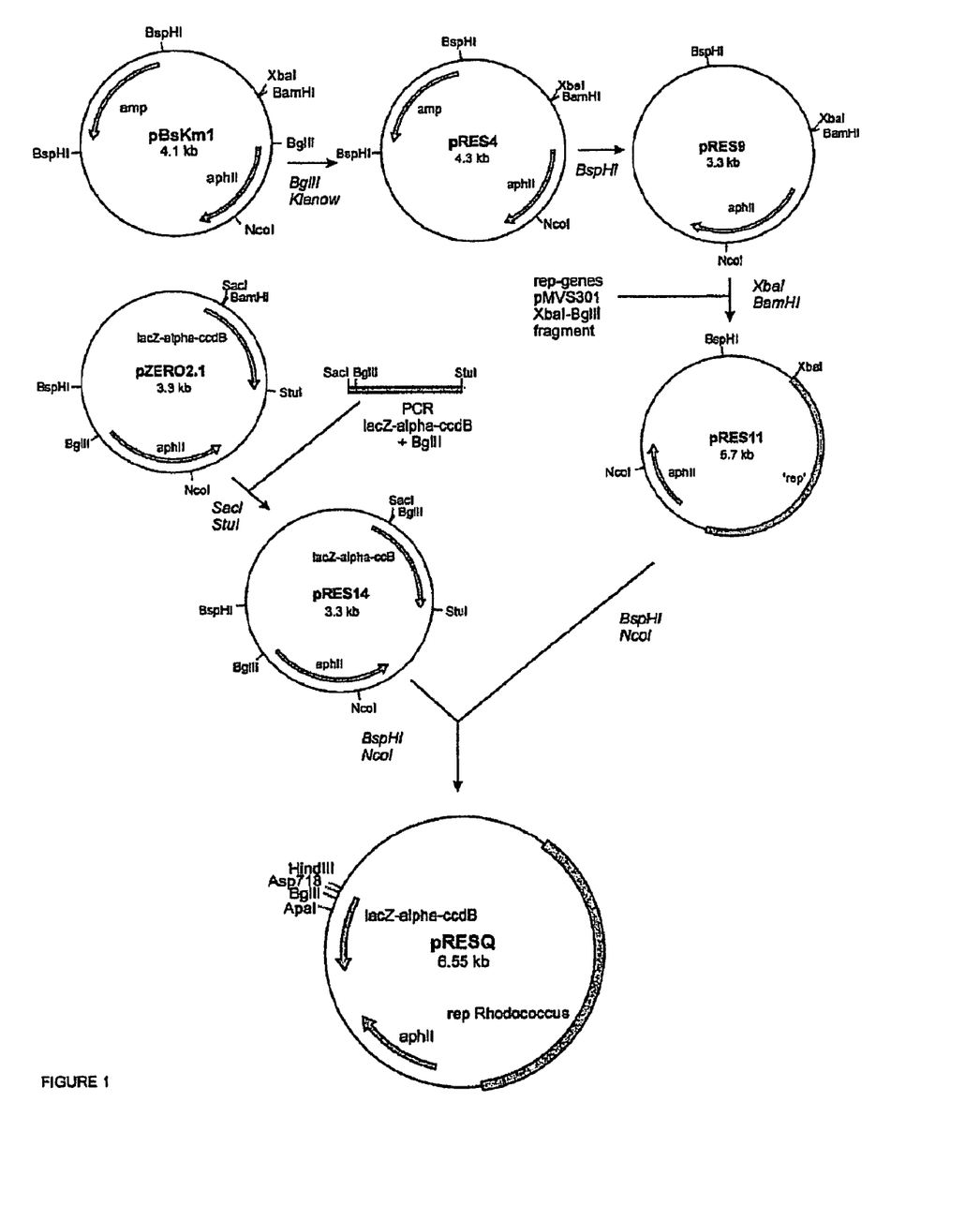
FIG. 1. The pZErO-2.1 (curved thin line) based *Rhodococcus*-*E. coli* shuttle vector pRESQ used for constructing a genomic library of *R. erythropolis* RG1.rep: 2.5 kb region of pMVS301 coding for autonomous replication in *Rhodococcus* sp (thick curved line). lacZ-ccdB: marker for positive selection in *E. coli*. aphII: kanamycin resistance marker for selection in *Rhodococcus* and *E. coli*.

For functional complementation of the KSH deficient mutant strains RG1-UV26 and RG1-UV39 and cloning of the kshA and kshB genes, a genomic library of *R. erythropolis* RG1 was constructed using *Rhodococcus-E. coli* shuttle vector pRESQ (FIG. 1). Sau3A digested chromosomal DNA of *R. erythropolis* RG1 was sized by sucrose gradient to 6–10 kb and ligated into BglII digested pRESQ. Transformation of *E. coli* Top10F' (Invitrogen Corp.) with this ligation mixture generated a gene library of approximately 15,000 transformants in which approximately 90% of the constructs contained insert. An average insert size of 6 kb was estimated. No complications with stability or rearrangements were apparent. The gene library represents the complete genome (p>0.99) assuming a genome size of approximately 6 Mb.

Figure 2:
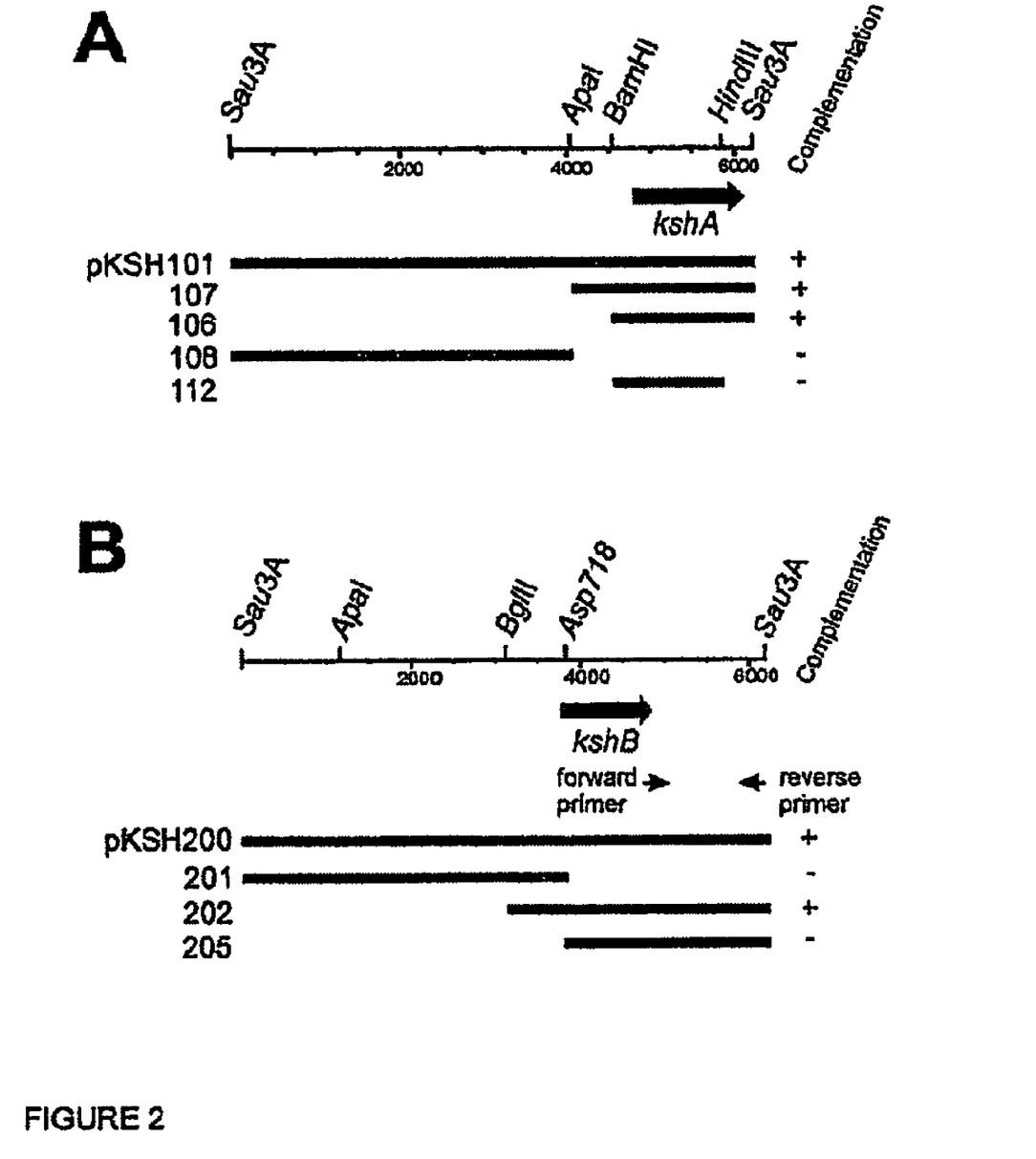
FIG. 2. Strategy for the separate cloning and identification of the kshA and kshB genes encoding KSH activity in *R. erythropolis* SQ1 by functional complementation of UV mutant strains RG1-UV39 (A) and RG1-UV26 (B), respectively, using several pRESQ derived constructs.

Introducing the *R. erythropolis* RG1 genomic library into strains RG1-UV39 and RG1-UV26 and subsequent screening for complementation of KSH deficiency, resulted in the cloning of two independent DNA fragments containing the ksh, gene and the kshB gene, respectively (FIG. 2).

Figure 3:
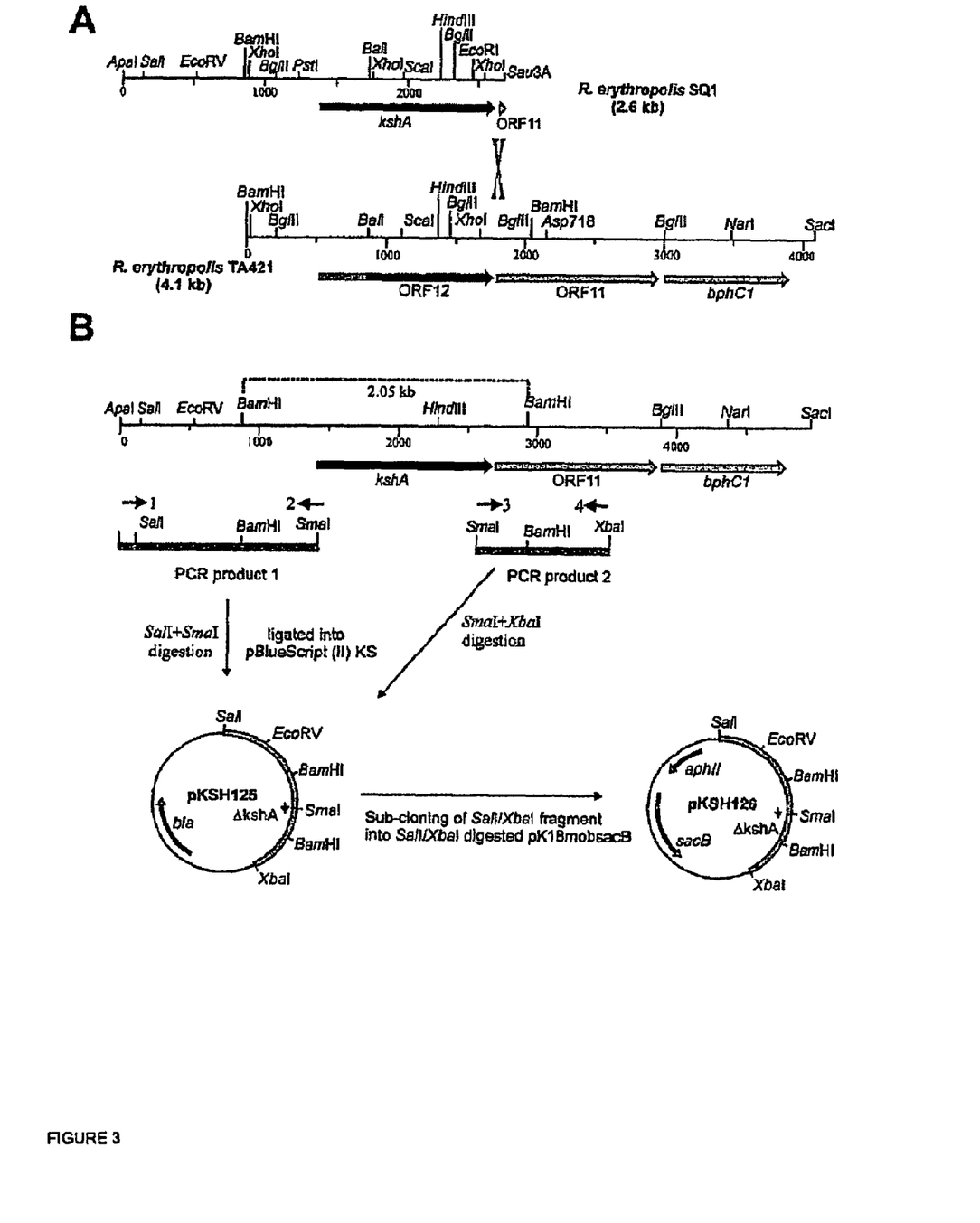

Analysis of these genes revealed that kshA encodes a 398 amino acid protein (KshA). KshA showed high similarity (58% identity; 84% similarity) to a hypothetical protein encoded by gene Rv3526 (DDBJ/EMBL/GenBank accession no. CAB05051) in *Mycobacterium tuberculosis* (Cole, S. T. et al Nature (1998) 393: 537–544). Rv3526 is thus expected to be the homologue of kshA in *M. tuberculosis*. Comparison of the obtained nucleotide sequence of ksha to databases further revealed that kshA is identical (97%) to a hypothetical gene (ORF12), found by Maeda, M. et al. (Appl. Environ. Microbiol. (1995) 61:549–555) in *R. erythropolis* strain TA421 (DDBJ/EMBL/GenBank accession no. D88013) upstream of bphC1 (FIG. 3). In analogy with the molecular organization found in strain TA421, a hypothetical ORF11, identified in this strain downstream of ORF12, was also identified downstream of kshA in strain SQ1. The nucleotide sequences of the DNA fragments of strain SQ1 and strain TA421 were therefore merged and the resulting theoretical nucleotide sequence was used for the successful construction of plasmid pKSH126 (FIG. 3) used for the introduction of an unmarked in-frame kshAA gene deletion in *R. erythropolis* strain SQ 1 (rendering strain RG2) and strain RG8 (rendering strain RG9).

The kshB gene encodes a 346 amino acid protein (KshB). Database similarity searches revealed that KshB showed high similarity to ferredoxinreductase components of multicomponent oxygenases. Highest similarity (56% identity; 85% similarity) was found with Rv3571 of *M. tuberculosis* (DDBJ/EMBL/GenBank accession no. A70606).

Inactivation of kshA or kshB by unmarked gene deletion renders molecularly defined and genetically stable mutant strains capable of selective $\Delta^1$-dehydrogenation of AD producing ADD that is not further metabolized due to absence of KSH activity (see WO 01/31050). Using the sacB counter selection system (described in WO 01/31050) three unmarked gene deletion mutant strains were constructed: a kshA mutant *R. erythropolis* RG2 using pKSH126 (FIG. 3), a kshB mutant *R. erythropolis* RG4 using pKSH212 (FIG. 4) and a kstD kstD2 kshA mutant *R. erythropolis* RG9. Strains RG2 and RG4 are derived from *R. erythropolis* SQ1. Strain RG9 is derived from kstD kstD2 mutant *R. erythropolis* RG8 using pKSH126 (FIG. 3). Strain RG8 lacks both 3-ketosteroid $\Delta^1$-dehydrogenase isoenzymes (KSTD1 and KSTD2; described in WO 01/31050).

Thus, another aspect of this invention is a microorganism blocked in 3-ketosteroid 9α-hydroxylase activity characterized in that it is a genetically modified microorganism, in particular of the family of Actinomycetales, preferably of the *Rhodococcus* genus and most preferred of *Rhodococcus erythropolis*. Also preferred is a strain, wherein at least one gene encoding 3-ketosteroid $\Delta^1$-dehydrogenase activity is inactivated, preferably by unmarked gene deletion. In particular preferred are the strains RG2, RG4 and RG9.

Also an aspect of the present invention is a method to construct a genetically modified strain of a steroid degrading microorganism lacking the ability to degrade the steroid nucleus, the method comprising inactivation of the genes encoding KSH-activity, preferably the gene ksh, and/or the gene kshb. Preferably, the inactivation of the gene(s) is accomplished by targeted, preferably unmarked, gene deletion.

A further aspect of the present invention is the use of a genetically modified microorganism in steroid $\Delta^1$-dehydrogenation, in particular in the preparation of 1,4androstadiene-3,17-dione and prednisolone. Preferably, the microorganism for such use has been obtained by targeted gene inactivation, preferably unmarked gene deletion, of the genes encoding KSH-activity in a microorganism of the family of Actinomycetales, preferably the gene kshA and/or the gene kshB. Preferred microorganism for this use is selected from the genetically-modified strains RG2, RG4 and RG9.

The micro-organism strains *Rhodococcus erythropolis* RG2, RG4 and RG9 have been deposited at the Deutsche Sammlung von Mikroorganismen und Zellkulturen GmbH (DSMZ), Mascheroder Weg 1b, D-38124 Braunschweig, Germany under the accession numbers DSM 14544, DSM 14545 and DSM 14546, respectively. These deposits have been made under the terms of the Budapest Treaty.

Methods to construct vehicles to be used in the mutagenesis protocol are well known (Sambrook et al., Molecular Cloning: a Laboratory Manual, Cold Spring Harbor Laboratory Press, Cold Spring Harbor, latest edition). Furthermore, techniques for site directed mutagenesis, ligation of additional sequences, PCR, sequencing of DNA and construction of suitable expression systems are all, by now, well known in the art. Portions or all of the DNA encoding the desired protein can be constructed synthetically using standard solid phase techniques, preferably to include restriction sites for ease of ligation.

Modifications and variations of the method for introducing disrupted gene mutations, targeted gene inactivation, and in particular unmarked gene deletion as well as transformation and conjugation will be obvious to those skilled in the art from the detailed description of the invention. Such modifications and variations are intended to come within the scope of present application.

A person skilled in the art will understand how to use the methods and materials described and referred to in this document in order to construct micro-organisms lacking KSH activity.

The following examples are illustrative for the invention and should in no way be interpreted as limiting the scope of the invention.

LEGENDS TO FIGURES

FIG. 3. (A) Overview of the 2.6 kb DNA fragment of *R. erythropolis* SQ1 encoding kshA and its 4.1 kb counterpart in *R. erythropolis* TA421. The grey bar of ORF12, together with the black arrow (proposed size of ORF12 by Maeda et al. (1995)), represents the actual size of ORF12 in *R. erythropolis* TA421, which is identical (97%) to kshA. The "X" indicates the point of merger of the two sequences. (B) Scheme of the theoretically merged nucleotide sequences of the DNA fragments of strain SQ1 and strain TA421, and its use in the construction of plasmid pKSH126 for unmarked in-frame kshA gene deletion in strain SQ1 and strain RG8. Numbers 1–4 indicate the primers used to obtain PCR products 1 and 2 for the construction of plasmid pKSH126 used for kshA unmarked gene deletion in parent strain SQ1 and kstD kstD2 mutant strain RG8.

EXAMPLES

General

Construction of the pRESQ Shuttle Vector

A pZErO-2.1 (Invitrogen Corp. San Diego, Calif.) derivative was constructed in which the BamHI site was replaced by a BglII site (FIG. 1). A SacI-StuI fragment of pZErO-2.1, containing the lacZ-ccdB gene, was duplicated by PCR using a mutagenic forward primer (5' ACC GAGCTCAGATCTACTAACGGC 3', SEQ D NO:3), containing the desired BglII restriction site (double underlined) and a SacI restriction site (underlined), and reverse primer (5' ATTCAGGCCTGACATTTATATTCCCC 3', SEQ D NO:4) with a StuI restriction site (underlined). The obtained PCR product was digested with restriction enzymes SacI and StuI and ligated in SacI-StuI digested pZErO-2.1 (PRES14). The aphII gene from pWJ5 (Jäger, W. A. et al. (1992). J Bacteriol 174:5462–5465) was cloned as blunted HindIII-BamHI fragment (Klenow fill in) into EcoRV digested pBlueScript (II) KS to construct pBsKm1. The unique BglII site in pBsKm1 was destroyed by BglII digestion followed by Klenow fill in (pRES4). The ampicillin cassette present in pRES4 was removed by self ligation following BspHI digestion (pRES9). A 2.5 kb BglII-XbaI fragment of pMVS301 (Vogt-Singer, M. F. et al., (1988) J. Bacteriol. 170:638–645), containing the region for autonomous replication in *Rhodococcus* sp., was subsequently ligated into BamHI-XbaI digested pRES9 to construct pRES11. Construction of pRESQ (6.55 kb) was completed by ligating a 4.15 kb BspHI/NcoI fragment of pRES11 into BspHI-NcoI digested pRES14.

Example 1

Inactivation of Steroid 9α-Hydroxylase Activity by UV Mutagenesis.

Late exponential phase *R. erythropolis* RG1(=kstD mutant) cells ($2 \cdot 10^8$ CFUs·ml$^{-1}$) grown in 10 mM glucose mineral medium were sonicated for a short period of time to obtain single cells. Diluted ($10^4$) samples were spread on glucose mineral agar medium and irradiated for 15–20 sec with a UV lamp (Philips TAW 15W) at a distance of 27 cm, on average resulting in 95% killing of cells. After 4 days of incubation, colonies that had appeared were replica plated on AD (0.5 g·l$^{-1}$ solubilized in DMSO (50 mg·ml$^{-1}$)) mineral agar medium. A screening for AD(D) growth deficient mutants of *R. erythropolis* RG1 able to grow on 9OHAD mineral medium yielded 2 mutants that were clearly impaired in the KSH reaction. These mutants, designated strain RG1-UV26 and strain RG1-UV39, showed no growth after 3–4 days with either AD or ADD as sole carbon and energy source, while growth on 9OHAD mineral agar medium was normal.

Example 2

Cloning and Molecular Characterization of kshA and kshB.

The *R. erythropolis* strain RG1 gene library was introduced into strain RG1-UV39 by electrotransformation to complement its mutant phenotype (FIG. 2). A clone was isolated containing a 6 kb insert (PKSH101) that was able to restore growth of strain RG1-UV39 on AD mineral agar medium. Restriction enzyme mapping analysis, subcloning in pRESQ and subsequent complementation experiments resulted in identification of a 1.8 kb BamHI-Sau3A DNA fragment (pKSH106) that was still able to complement strain RG1-UV39 (FIG. 2). This 1.8 kb insert was cloned into pBlueScript (II) KS and its nucleotide sequence determined. Nucleotide sequence analysis revealed a single 1,197 nt ORF (kshA, 499–1695 of SEQ ID NO:1) encoding a putative protein of 398 aa (KshA).

Complementation of *R. erythropolis* RG1-UV26 with the strain RG1 gene library resulted in isolation of clone pKSH200 able to restore growth of strain RG1-UV26 on AD mineral agar medium (FIG. 2). By subsequent restriction mapping analysis, subcloning and complementation experiments of pKSH200 we identified a 2.8 kb BgIU-Sau3A fragment (pKSH202) which was still able to restore the mutant phenotype of strain RG1-TV26 (FIG. 2). This fragment was subcloned into pBlueScript (II) KS and its nucleotide sequence was determined. The ORF responsible for complementing the RG1-UV26 mutant phenotype was identified from a subsequent complementation experiment. An Asp718 restriction site mapped on the 2.8 kb fragment was used to construct pKSH205, which could no longer complement the mutant phenotype (FIG. 2). The Asp718 restriction enzyme thus is located within the ORF responsible for complementation. The identified ORF of 1,041 nt was designated kshB (387–1427 of SEQ ID NO:2; GC content, 62.3%) encoding a putative protein of 346 amino acids with a calculated molecular weight of 37.1 kDa (KshB).

Example 3

Unmarked Gene Deletion of kshA in *R. Erythropolis* SQ1.

For unmarked in-frame gene deletion of kshA (ΔkshA) pKSH126 was constructed. A 1.3 kb fragment (PCR product 1) was obtained from pKSH101 using a primer (FIG. 3 primer 1) annealing to sequences upstream of kshA (5' CGCGGGCCCATCGAGAGCACGTT 3', SEQ ID NO:5), and a primer (FIG. 3 primer 2) annealing to the 5'-end of the kshA gene (5' GCGCCCGGGTCCGAGTGCCATGTCTTC 3', SEQ ID NO:6) containing a SmaI site (underlined). Primers for PCR product 2 were developed using the nucleotide sequence of the merged sequences of strain SQ1 and strain TA421 (DDBJ/EMBL/GenBank accession no. D88013). PCR product 2 (840 bp) was obtained from SQ1 chromosomal DNA using forward primer (FIG. 3 primer 3) annealing to the 3' end of the kshA gene (5' GCG CCCGGGACAACCTCCTGATTCGCAGTC 3', SEQ ID NO:7), including a SmaI restriction site (underlined), and reverse primer (FIG. 3 primer 4) annealing to ORF11 (5' GCGTCTAGAGTGGAAGAGCATTCCCTCGCA 3', SEQ ID NO:8), including a XbaI restriction site (underlined). The SmaI restriction site was introduced to give an in-frame deletion of kshA following ligation of this PCR fragment behind the 5'-truncated kshA gene from PCR product 1. Finally, a 2.05 kb SalI-XbaI fragment from pKSH125 was ligated into pK18mobsacB vector (pKSH126).

Unmarked in-frame deletion of the kshA gene was obtained by introducing the mutagenic vector pKSH126 in strain SQ1 followed by sacB counter selection (WO 01/31050). Wild type kshA gene was reduced to an ORF (ΔkshA) of 30 nt, encoding only 9 amino acids (MALG-PGTTS). Gene deletion of kshA was confirmed by Southern analysis of BamHI digested chromosomal DNA using the 2 kb insert of pKSH126 as a probe: a 2.05 kb wild type BamHI DNA fragment was reduced to 0.88 kb in the gene deletion mutant strains. The resulting strain is designated *R. erythropolis* RG2.

Example 4

Unmarked Gene Deletion of kshB in *R. Erythropolis* SQ1.

Figure 4:
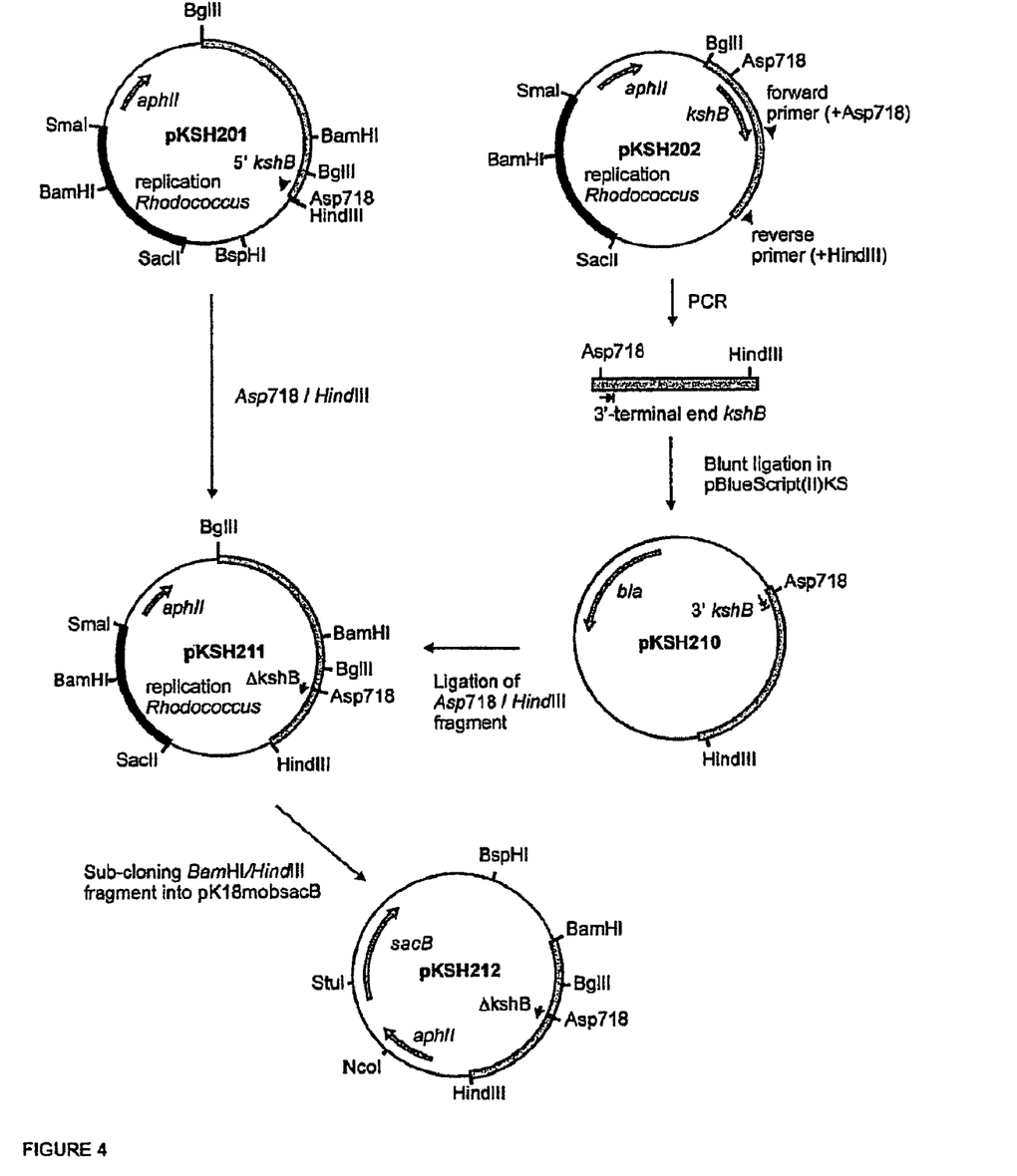
FIG. 4. Cloning scheme for the construction of plasmid pKSH212 used in the construction of kshB unmarked gene deletion mutant strain RG4 from parent strain SQ1.

For unmarked in-frame gene deletion of kshB construct pKSH212 was made (FIG. 4). For this purpose pKSH201 was fused to a PCR product (1,275 bp) obtained from pKSH202 as a template. PCR product was obtained with forward primer 5' GCGGGTACCGATCGCCTGAAGATC-GAGT 3' (SEQ ID NO:9) and reverse primer 5' GCGAAGCTTGCCGGCGTCGCAGCTCTGTG 3' (SEQ ID NO:10) and ligated (blunt) into EcoRV digested pBlueScript(II) KS (pKSH210). At the 5'-terminal end of this PCR product an Asp718 restriction site, preceding the stop codon of kshB (see forward primer), was introduced to ensure proper in-frame deletion of kshB after ligation with the Asp718 restriction site of pKSH201. At the 3'-terminal end a HindIII restriction site (see reverse primer) was added, compatible to the HindIII restriction site of pKSH201, for cloning purposes. PCR product was isolated from pKSH210 by Asp718-HindIII digestion (1,263 bp) and ligated into Asp718-HindIII digested pKSH201 (FIG. 2) pKSH211), thereby introducing the desired kshB in-frame deletion (FIG. 4). Finally, a BamHI-HindIII DNA fragment (2.2 kb) containing the kshB deletion was ligated into pK18mobsacB (see WO 01/31050) digested with BamnHI and HindIII (pKSH212).

Plasmid pKSH212 was introduced into *R. erythropolis* SQ1 by conjugation using *Escherichia coli* S17-1. Unmarked kshB gene deletion was obtained using the sacB counter selectable system (WO 01/31050). Potential kshB mutants were screened by replica plating on AD mineral agar plates, which enabled us to isolate kshB mutants unable to grow on AD. Southern analysis was performed on Asp718 digested chromosomal DNA of wild type and three AD growth deficient mutants. Hybridization with the complete kshB gene showed that kshB was not present in the genome of the putative kshB mutants. A clear hybridization signal (4.3 kb fragment) was exclusively found with wild type chromosomal DNA. Additional Southern analysis with an alternative probe, being the 2.2 kb insert of pKSH212 comprising both flanking regions of kshB, furthermore confirmed kshB gene deletion: a 4.3 kb Asp718 wild type DNA fragment containing the kshB gene was reduced to 3.3 kb in a kshB mutant, demonstrating replacement of the 1,041 bp kshB gene by a kshB in-frame remnant of 30 nt (encoding MTTVEVPIA). The resulting strain is designated *R. erythropolis* RG4.

Example 5

Use of a Genetically Modified Strains RG1-UV26, RG1-UV39, RG2, RG4 and RG9 in steroid $\Delta^1$-dehydrogenation.

Strains RG2 and RG4 were plated on mineral agar media containing AD, ADD or 9OHAD as sole carbon and energy source. Both strains showed no growth on AD(D), whereas growth on 9OHAD was comparable to strain SQ1. These phenotyps are in agreement with those found with UV mutant strains RG1-UV26 and RG1-UV39. Bioconversion of AD (1 g·l$^{-1}$) with strain SQ1 results in AD utilization but not in accumulation of ADD or other metabolites. Bioconversion of AD (1 g·l$^{-1}$) by strain RG2 or strain RG4 resulted in comparable accumulation levels of ADD (varying between 0.3–0.5 g·l$^{-1}$ after 168 h). AD(D) 9α-hydroxylation thus is blocked by inactivation of either kshA or kshB, demonstrating the essential role of both KshA and KshB in KSH activity in *R. erythropolis* SQ1. In AD bioconversion experiments with strain RG9, neither a decline in the initial AD concentration nor 9OHAD formation was observed. Mutant strain RG9 thus confirms that kshA encodes AD 9α-hydroxylase activity and that, contrary to the KSTD isoenzymes, no further KSH isoenzymes are present in *R. erythropolis* SQ1.

We claim:

1. An isolated polynucleotide sequence comprising a nucleic acid sequence selected from the group consisting of:
   a first nucleic acid encoding the KshA protein encoded by nucleotides 499–1695 of SEQ ID NO:1 and
   a second nucleic acid having at least 98% identity with the entire DNA sequence of the nucleotides 499–1695 of SEQ ID NO:1, wherein the second nucleic acid encodes a protein that retains the 3-ketosteroid 9α-hydroxylase activity of the KshA protein.

2. The polynucleotide sequence of claim 1 comprising a nucleic acid sequence selected from the group consisting of SEQ ID NO:1 and nucleotides 499–1695 of SEQ ID NO:1.

3. The polynucleotide sequence of claim 1 consisting of the nucleic acid sequence SEQ ID NO:1.

4. An isolated polypeptide encoded by the nucleic acid sequence comprising nucleotides 499–1695 of SEQ ID NO:1.

* * * * *

SEQUENCE LISTING

<160> NUMBER OF SEQ ID NOS: 10

<210> SEQ ID NO 1
<211> LENGTH: 1770
<212> TYPE: DNA
<213> ORGANISM: Rhodococcus erythropolis SQ1

<400> SEQUENCE: 1

```
ggatccgtga ggccgctggg ctcgactctc gagcggatca ccgaatacca cgaccagacc      60
gggcatctgg ttgccgaggt cttcgtccgg gaagccccga cagcgggcac cggaaccgat     120
tccgttgctg cccttgccga tttcgccgct cgtcgttacg gctcggcgtc gctacgacgg     180
ttccgcggac gttgcaccgc aacttccgcg ggagcagatc tgaactgctc cgtgacggtg     240
ctcgctacgt acgagaagga ccacgagagc gtcgccgacg tagctctggt cgccaccgat     300
cccaccgggg tcgtcaccgc tcgggcctgg gcgacttacg cgatcgacga tgtggcgaca     360
ctcgcgagct gaatctctgc aggtcaccga gcggtgttc catccagcgg gaactgccgt     420
atctccagag gacgcttcgt cgttgtatga gacggatcac atcactggag cgtcgcaaga     480
cgcggctcgg aggaagacat ggcactcgga accggcccac tcaccactac ggacgcctcg     540
acgcagtcgg gcgccggcga ggaaattcga gaaatcgaag cggcagcgcc cccggcgcgg     600
ttcgcgcgtg gatggcactg cctcggactg agcaatacct atcgcgacgg tcagccccac     660
cagatcgagg cattcggcac cagccttgtc gtcttcgccg acagcaaggg cgacatcaag     720
attctcgacg cctactgccg ccacatgggt ggcaacctcg ctcacggaac cgtcaagggc     780
gattcgatcg cctgcccgtt ccacgactgg cgttggggcg gtaacggaaa atgtacggcg     840
atcccctacg cacgacgcgt tccgccgctg gccaagacgc gggcgtggac cacactcgag     900
aagaacggtc agctgttcgt ctggcacgat ccccagggga atccccgcc cgccgaggtc     960 acaattcccg acatcgaggg cttcggaagc gatgagtgga gcgactggag ctggaatacg    1020
ctcaccatcg aaggctctca ttgccgcgag atcgtggaca acgtcgtgga catggcccac    1080
ttcttctacg ttcactactc gttccccaag tacttcaaga acatcttcga aggtcacgta    1140
gcgagccagt acatggaatc ggtgggacgc gaggacatca tcagcggcac caactacggc    1200
gatcccaacg ctgttcttcg ttcggatgct tcgtatttcg gtccgtcgta catgatcgac    1260
tggatcaaga gcgaagccaa cgggcagatc atcgaaactg tattgatcaa ctgccactac    1320
cccatctcga acaatgcctt cgtgttgcag tacggcgcga tggtcaagaa gcttcccggt    1380
atggacgacg agtccactgc cgcgatggcc gcgcagttca ccgagggcgt cgagatggga    1440
ttccttcagg acgtggagat ctggaagaac aaggcccccga tcgacaaccc gctgctctcg    1500
gaggaggacg gcccggttta ccagttgcgg cgctggtaca accagttcta caccgatgtc    1560
gagaacgtca cggaagacat gacgaagcgc ttcgaattcg agatcgacac tacccgcgca    1620
gtggagagct ggaagcggga agtcgccgaa aacgttgccg cacgtgacgc ccaggcgctc    1680
```

```
gagacaacct cctgattcgc agtcgaaaac actgctgaga caacctgact gaacgcaagg    1740
aacaacatga cgtacgaagt gctcgaacag                                     1770

<210> SEQ ID NO 2
<211> LENGTH: 1500
<212> TYPE: DNA
<213> ORGANISM: Rhodococcus erythropolis SQ1

<400> SEQUENCE: 2
agatctggtt gagctcgata gccatcggta tctcctcatg gatgtgcacg aatgtgactg      60
cgggagggat tcgagccgat tctttgtgac cggcgtctca cctggttccc actgtgtacc    120
gacaaacacc ccgtgcacag acttcggcag ctcaaccgcc cggacgccgc ccgcgaaccg    180
cccgttcggg caggtcgtcg ccaccccgga ccgccaggaa ggccggatca gactgccgtg    240
gttcccgctg atcgggaacg tgttgctcgg cgactacgat ccccagtagc ttttcatcac    300
tgctaacatt gaactagaac acgttctaga tgttgcactt cactgacctg cgctttaccc    360
agcttcacga gaggactagc ttcgcgatga cgacagtcga ggtaccgcac agctcgcgat    420
cggcggtact caccgtgtcc ggagtcatcg aagagacttc cgacgcccgg tcgctggtgt    480
tcgagattcc cgcagaactg aaggacaagt tcgactacaa gccaggtcaa ttcctgaccc    540
tgcgcatccc gagtgatcaa accggctcgg tcgcacgctg ctactccctg gccagttcac    600
ccttcaccga cgacgccccc aaggtgacct caagcgaac cgtcgacggc tacggctcca    660
actggttgtg cgacaagctc caggtcggcg acaccatcga agtgctgccg ccgtcaggtg    720
tcttcacgcc caaatcgctc gatcacgact cctgctctct cggtgcaggc agcggaatca    780
ctccggtgat ctcgattctc aagtccgccc tcacacaggg cagcggcaat gtcgtgctga    840
tctacgcgaa tcgcgacgag aagtccgtca tcttcggcgc cgaactgcgc gagctggcag    900
cgcaacaccc cggccgcctc accgtggtcc actggatcga aaccgtgcag ggactccccg    960
ctgtctcaca actggcgacg ctcgccaagc cttttgtcgc gtacgaggcc ttcatgtgcg   1020
gtccaggccc tttcatggac gccgtccaca aggcactggc agaagcgggc atgcccgca   1080 cgcaggttca cgccgaggtc ttcaattcac tcgccggcga cccgttccgt gacgtcgagg   1140
tagcagaggt ctccgacgag gaagctgccg acgccgcaac cgtcgaggtc gaactggacg   1200
gtgaaaccca caccctcgtc tggccgcgca gcagacgct cgtcgacatc atgctcgcaa   1260
agggtctcga cgttccgtac tcctgcaagg aaggtgagtc cgggtcgtgt gcctgcaccg   1320
tcaccgaagg cgaagttcag atggacaact ccgagatcct cgacgccgag gacgtggcga   1380
acggctacat cctcggttgc aagcgaagcc gatcaccgat cgcctgaaga tcgagtctga   1440
accctgcttc gatgcatgac ggccccttga ttccctgcgg aatcgggggc tttgtcatct   1500

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 3
accgagctca gatctactag taacggc                                         27

<210> SEQ ID NO 4
<211> LENGTH: 26
<212> TYPE: DNA
```

<213> ORGANISM: Artificial Sequence
<220> FEATURE:
<223> OTHER INFORMATION: Description of Artificial Sequence:primer

<400> SEQUENCE: 4
attcaggcct gacatttata ttcccc                                26

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 5
cgcgggccca tcgagagcac gtt                                  23

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 6
gcgcccgggt ccgagtgcca tgtcttc                              27

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 7
gcgcccggga caacctcctg attcgcagtc                           30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 8
gcgtctagag tggaagagca ttccctcgca                           30

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence:primer

<400> SEQUENCE: 9
gcgggtaccg atcgcctgaa gatcgagt                             28

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence:primer

```
<400> SEQUENCE: 10
gcgaagcttg ccggcgtcgc agctctgtg                                  29
```